United States Patent
Nam et al.

(10) Patent No.: US 9,821,354 B2
(45) Date of Patent: Nov. 21, 2017

(54) METHOD FOR REMEDIATING CONTAMINATED SOIL USING MICROORGANISM STRAIN HAVING ABILITY TO PRODUCE UREASE

(71) Applicant: KOREA INSTITUTE OF GEOSCIENCE AND MINERAL RESOURCES (KIGAM), Daejeon (KR)

(72) Inventors: In Hyun Nam, Daejeon (KR); Jae Gon Kim, Daejeon (KR); Chul-Min Chon, Daejeon (KR); Min-Jeong Park, Daejeon (KR)

(73) Assignee: KOREA INSTITUTE OF GEOSCIENCE AND MINERAL RESOURCES (KIGAM), Daejeon (KR)

( * ) Notice: Subject to any disclaimer, the term of this patent is extended or adjusted under 35 U.S.C. 154(b) by 0 days.

(21) Appl. No.: 15/203,034

(22) Filed: Jul. 6, 2016

(65) Prior Publication Data

US 2017/0008052 A1    Jan. 12, 2017

(51) Int. Cl.
*C12N 9/80* (2006.01)
*B09C 1/08* (2006.01)
*B09C 1/10* (2006.01)

(52) U.S. Cl.
CPC ............... *B09C 1/08* (2013.01); *B09C 1/105* (2013.01); *C12N 9/80* (2013.01); *C12Y 305/01005* (2013.01); *B09C 2101/00* (2013.01)

(58) Field of Classification Search
None
See application file for complete search history.

*Primary Examiner* — Mindy G Brown
(74) *Attorney, Agent, or Firm* — Ladas & Parry LLP; Loren K. Thompson

(57) ABSTRACT

The present invention provides a method of remediating contaminated soil with heavy metal using a microorganism of *Sporosarcina* sp. Contaminated soil is inoculated with the *Sporosarcina* sp. KM-01 (*Sporosarcina pasteurii* KM-01) strain includes a base sequence of SEQ ID NO. 1, the *Sporosarcina* sp. KM-07 (*Sporosarcina pasteurii* KM-07) strain includes a base sequence of SEQ ID NO. 2, and the *Sporosarcina* sp. KM-12 (*Sporosarcina pasteurii* KM-12) strain includes a base sequence of SEQ ID NO. 3. The strains are capable of producing urease.

20 Claims, 5 Drawing Sheets

METHOD FOR REMEDIATING CONTAMINATED SOIL USING MICROORGANISM STRAIN HAVING ABILITY TO PRODUCE UREASE

BACKGROUND

The present invention disclosed herein relates to a method for remediating contaminated soil, and more particularly to a method for remediating contaminated soil, which has acidic property and is contaminated with heavy metals, in an exhausted mine area by using a biological and biochemical method.

Exhausted mine areas have been neglected for a long period of time without appropriate treatment of environmental contamination after mining activities such as digging, cradling, and refining. In the exhausted mine areas, severe contamination in soil and a water system of stream occurs due to release of acidic mine drainage, loss of mine tailings caused by rainfall, and spread of dust derived from mine wastes, etc.

In particular, it has been reported that arsenic, cadmium, copper, lead, and aluminum contamination levels in metalliferous mine areas are high. Moreover, in about 50% or more of the total exhausted mine area, a soil contamination level of surrounds exceeds a concern level.

To remediate the soil contaminated with heavy metals, a study has been continuously conducted to improve and neutralize acidic soil by employing, as a soil stabilizer, an alkaline material such as limestone ($CaCO_3$), and slaked lime ($Ca(OH)_2$), metal oxides of Fe, Al, and Mn, clay, phosphate, compost, red mud, and alum sludge.

Among the above materials, a carbonate mineral (e.g., limestone) particularly has an effect of buffering an acidic reaction according to oxidation, thereby increasing pH of contaminated soil and precipitating metal ions in an oxide- or sulfate hydroxide form. Therefore, calcium carbonate has been widely used as a neutralizer and a heavy metal stabilizer in the acidic soil contaminated with heavy metals.

Typically, remediation of soil has been conducted through the method of directly spreading limestone including calcium carbonate as a main ingredient to contaminated soil. However, spreading calcium carbonate once does not bring to a significant effect. Nonetheless, periodically spreading calcium carbonate for a long period of time is not economical.

SUMMARY

An object of the present invention is to provide a method for remediating contaminated soil by spreading, to exhausted mine areas, urease extracted from a plant and a microorganism strain of *Sporosarcina*. sp capable of producing urease to precipitate calcium carbonate in the soil.

To solve the problems above, the present invention uses a microorganism strain. When inoculating soil contaminated with heavy metals with the microorganism strain, the microorganism strain produces urease which is an enzyme degrading urea in the soil. The urease degrades urea in the soil to thereby generate a carbonate ion. The carbonate ion binds to a calcium ion in the soil to thereby precipitate calcium carbonate in the soil. During the course of calcium carbonate formation, heavy metals are coprecipitated with or adsorbed in calcium carbonate, so that mobility of heavy metals is declined. Calcium carbonate fills pores in the soil to thereby make soil become rigid, and thus the soil is prevented from loss due to rain and wind. Also, an ammonium ion generated during degradation of urea neutralizes acidic soil. In the present invention, together with the microorganism strain, urease extracted from bean juice may be separately provided to the soil. In preparation for the case where urea and calcium in soil are insufficient, a urea agent and calcium agent may be additionally provided. Also, the microorganism strain, urease, urea agent and calcium agent are mixed in a composition form and then the composition is provided to soil.

The present invention uses *Sporosarcina* KM-01 strain including a base sequence of SEQ ID NO: 1, *Sporosarcina* KM-07 and *Sporosarcina* KM-12 strain. These strains are respectively deposited on Apr. 27, 2015 and registered to Korea Collection for Type Cultures (KCTC) of the Korean Research Institute of Bioscience and Biotechnology (KRIBB) International Depository Authority, at 125 Gwahak-ro, Yuseong-gu, Daeleon 305-806, Republic of Korea, in compliance with the Budapest Treaty on the International Recognition of the Deposit of Microorganisms for the Purpose of Patent Procedure as Deposit Accession numbers KCTC 12800BP, KCTC 12801 BP and KCTC 12802BP. The present inventors hereby assure the United States Patent and Trademark Office and the public that (a) all restrictions on the availability to the public of the deposited material described above will be irrevocably removed upon issuance of a United States patent of which any of such deposited material is the subject; (b) the deposited material will be maintained for a period of at least five years after the most recent request for the furnishing of a sample of any of the deposited material was received by the KCTC and, in any case, for a period of at least 30 years after the date of deposit or for the effective life of such patent, whichever is longer; (c) should any of the deposits become non-viable or mutated, or otherwise incapable of being furnished by the depository upon request due to the condition of the deposit, it will be replaced by Applicants; and (d) access to the cultures will be available to the Commissioner during the pendency of the patent application or to one determined by the Commissioner to be entitled to such cultures under 37 C.F.R. §1.14 and 35 U.S.C. §122.

The *Sporosarcina* sp. strain according to the present invention may be isolated from soil having acidic property and contaminated with heavy metals in exhausted mine areas.

BRIEF DESCRIPTION OF THE DRAWINGS

FIG. 5 is a photo of $CaCO_3$ produced by urease produced by 3 strains taken with an electron microscope (SEM) and a table showing EDS element analysis result.

DETAILED DESCRIPTION OF PREFERRED EMBODIMENTS

Figures 1, 2:
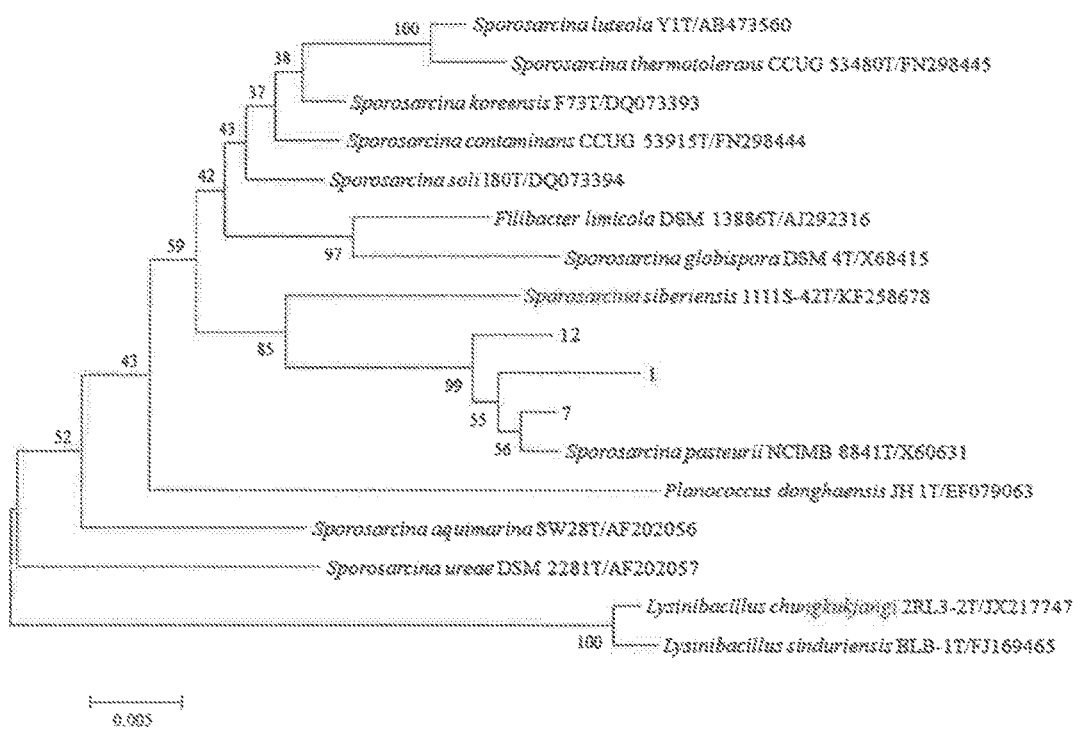
FIG. 1 shows a result of preparing a phylogenetic tree for 3 strains isolated from an exhausted mine.
FIG. 2 is a table showing heavy metal concentration in a soil sample, and pH and EC of the soil sample.

Hereinafter, the present invention will be described in more detail.

The present invention is to remediate contaminated soil by inoculating acidic soil, which is contaminated with heavy metals, with a novel microorganism strain capable of producing urease.

The novel microorganism strain used in the present invention may be derived from soil in areas contaminated with heavy metals, for example an exhausted mine area. Also, as a result of molecular biological identification through analysis of morphological characteristic, metabolic activity, physiological characteristic, and 16S rRNA sequencing, the microorganism strain is found to be a *Sporosarcina* sp. strain (*Sporosarcina pasteurii*).

The novel strains used in the present invention are 3 types: a *Sporosarcina* sp. KM-01 strain having a base sequence of SEQ ID NO: 1; a *Sporosarcina* sp. KM-07 strain having a base sequence of SEQ ID NO: 2; and a *Sporosarcina* sp. KM-12 strain having a base sequence of SEQ ID NO: 3. These strains are respectively registered to Korea Collection for Type Cultures (KCTC) with information of SEQ ID NOS: 1, 2, and 3. The KM-01 strain is registered under accession number KCTC number 12800BP. The KM-07 strain is registered under accession number KCTC 12801BP, and the KM-12 strain is registered under accession number KCTC 12802BP. In addition, appended base sequences of strains are defined with sequence listings 1, 2 and 3 and appended to the present specification. For convenience of the explanation, the 3 novel strains are respectively referred to as KM-07 strain, KM-12 strain and KM-01 strain. For collectively calling these 3 strains, the strains are referred to as a *Sporosarcina* sp. strain.

The novel *Sporosarcina* sp. strain used in the present invention may be obtained by collecting soil in an exhausted mine area contaminated with heavy metals, placing the resultant in a urea medium and culturing, and then isolating a single colony from the strain and pure culturing the strain.

These strains are used for 3 purposes. That is to say, the strains may be used for 3 purposes as follows: stabilization caused by decline in mobility of heavy metals in soil; soil reinforcement and soil loss prevention through caking of the soil; and neutralization of acidic soil. Remediation of contaminated soil means that transfer of heavy metals in soil is prevented; acidic soil is neutralized; and soil is prevented from loss by caking the soil. Depending on contamination degrees of soil, the strains may be used for only one purpose among the purposes described above. However, in an exhausted mine area where a main subject of the present invention, heavy metal contamination, soil acidification and soil loss occur together.

The three purposes described above are achieved through calcium carbonate precipitation. Even though it will be described in more detail below, the *Sporosarcina* sp. strain produces urease in an environment where urea exists, thereby hydrolyzing urea into a carbonate ion and ammonium ion. The carbonate ion reacts with a calcium ion in soil to thereby precipitate calcium carbonate.

The first purpose, i.e. stabilization of heavy metals, and the second purpose, i.e., soil reinforcement are achieved during the course of calcium carbonate precipitation. That is to say, when calcium carbonate is precipitated, heavy metals having a micro particle size are stabilized by being co precipitated with or adsorbed in calcium carbonate. The term "stabilization" used herein means that a probability in which heavy metals are dissolved in acidic water such as rainwater or leachate in mines and transferred together is decreased.

Further, calcium carbonate fills pores in soil, thereby increasing strength of the soil, so that soil is caked. Through this, soil may be stabilized and soil loss may be prevented. Prevention of soil loss has significance in terms of decline of transfer of heavy metals. That is because heavy metals are transferred together when soil is transferred due to wind.

The last purpose, i.e., neutralization of acidic soil is achieved by an ammonium ion which is a hydrolyzed product of urea. The ammonium ion has basicity, thereby increasing pH of soil. When pH of soil is increased by the ammonium ion, an effect of promoting calcium carbonate precipitation is concomitant.

Examples of heavy metals stabilized by the *Sporosarcina* sp. strain include manganese, arsenic, zinc, copper, and lead, etc. In addition to those described above, various heavy metals may be included. As described above, since stabilization of heavy metals means coprecipitation and adsorption of heavy metals during calcium carbonate precipitation, stabilization may be applied to various heavy metals without being limited by types of heavy metals.

In the method for remediating contaminated soil according to the present invention, any one of the methods as follows may be selected: a method of inoculating soil with the KM-01 strain alone; a method of selecting either KM-07 strain or KM-12 strain and inoculating the selectant with the KM-01 strain; or a method of inoculating with 3 strains all together. Even though there are little differences in activities and abilities to precipitate $CaCO_3$ among the strains, each of the strain alone is capable of sufficiently producing urease in an environment where urea exists, and precipitating calcium carbonate. In particular, the KM-01 strain has the most excellent ability to produce calcium carbonate.

Specifically, a composition, which contains, as an active ingredient, the KM-01 strain alone or a mixture in which the KM-01 strain is mixed with the KM-07 strain and KM-12 strain, for remediating contaminated soil is prepared.

In addition, the composition for remediating contaminated soil may additionally include a urea ingredient. In the case where contaminated soil to be remediated has sufficient urea, the composition including only the strains is used and urea in the soil is used. However, in the case where soil does not include urea, a urea agent is preferably added. Further, a calcium agent is generally included in most soil, however in the case where there is no calcium agent, a calcium agent such as calcium chloride may be added to the composition for remediating contaminated soil.

Further, without being prepared in a composition form, urea is provided to soil, and then the microorganism strain may be inoculated. Separately, a calcium agent may be provided. These processes may be performed sequentially or concomitantly.

In the preparation for shortage of urease production by the microorganism strain, in the present invention, urease may be additionally provided. The urease may be extracted from a plant, e.g., bean juice.

Hereinafter, embodiments of the present invention will be described in more detail.

Some microorganisms present in soil induce urease (i.e., an enzyme degrading urea) in an environment where urea and calcium exist, thereby producing mineral materials such as calcium carbonate in surrounding areas. In other words, microorganisms produce urease due to metabolic activities, and the urease hydrolyzes 1 mole of urea to generate 2 mole of ammonium ion and 1 mole of carbonic acid as the following equation (1). Then, the carbonate ion causes a reaction of precipitating calcium carbonate to occur with a calcium ion provided by a calcium source (e.g., calcium chloride) present in the soil as the following equation (2).

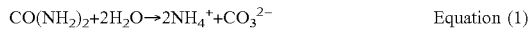 Equation (1)

 Equation (2)

It has been reported that urease is found in plants and some bacteria, and, in particular, bacterial urease plays an important role in environmental transition of nitrogen compounds such as a nitrogen cycle in farmlands or nitrogen metabolism of ruminants in environmental ecosystems. The bacterial urease genes include at least 7 genes having similar structural arrangement, and are divided into structural proteins (i.e., UreA, UreB and UreC) and accessory proteins (i.e., UreD, UreE, UreF and UreG). The structural protein serves a key role in the enzyme activity, and the accessory protein serves combination and transfer of $Ni^{2+}$ to the structural protein. Generally, bacterial urease has a molecular weight of 200-250 kD.

The researchers of the present invention have been conducted a study about periodically providing urease extracted from a plant to contaminated soil. However, there is a problem in that urease should be periodically provided for a long period of time. Therefore, soil is inoculated with bacteria capable of producing urease in order to achieve a continuous and stable remediation of soil. Surely, by additionally providing urease extracted from a plant (bean juice) separated from the microorganism strain, the effect may be enhanced.

Since the bacteria capable of producing urease should maintain the activity in contaminated soil, an object of the present invention is to isolate a microorganism having an ability to produce urease from contaminated soil.

Therefore, the researchers of the present invention select a strain which exists in contaminated soil in an exhausted mine area and has a strong urease activity, and then investigate and observe micrological and biochemical characteristics of the strains.

1. Experimental Process (1) Isolation and Identification of Strain and Investigation of Growth Rate To isolate a bacterial strain, 30 g of soil surrounding a mine head of an exhausted metalliferous mine located at Busan was collected and placed in a sterilized Falcon tube. In the present invention, as a medium for isolating and identifying a bacteria producing urease, a urea medium (2% yeast extract, 1% $NH_4Cl$, 0.3% NaCl, 2% urea) was used. As a solid medium, a urea medium containing 1.5% agar was used. To isolate a strain producing urease from collected samples, 1 g of collected soil was added to 99 mL of urea liquid medium, and the resultant was suspended for 48 hours in a shaking incubator (160 rpm, 28° C.). The suspension was diluted with 20 mM phosphate buffer (pH 7.0), and spread to the urea solid medium. Then, the resultant was subjected to static culture at 28° C. for 24 hours. About 20 types of various colonies were inoculated to the urea solid medium, and then each of the strain was subjected to pure isolation. Among these, a base sequence of 16S rRNA gene of a colony obtained through pure isolation of a strain having a urease activity was sequenced. As a primer, SEQ ID NO: 4 which corresponds to the laboratory arbitrary label of 518F (5'-CCA GCA GCCGCG GTA ATA CG-3') and SEQ ID NO: 5 which corresponds to the laboratory arbitrary label of 800R (5'-TAC CAG GGT ATC TAATCC-3') were used. The analyzed base sequence was compared to "Gene Bank database" through "Basic Local Alignment Search Tool (BLAST)" algorism of "The National Center for Biotechnology Information (NCBI)" to identify the isolated microorganism. The analyzed 16S rRNA gene base sequences were aligned by using "Bioedit (Ver. 7.0)". The 16S rRNA gene sequence used in phylogenetic analysis was based on NCBI data base. For the phylogenetic tree, 1,000 times of bootstrap analysis was performed by using the "neighbor-joining method" using the MEGA (Ver. 6.0) program to perform relation analysis of microorganism species.

To evaluate the growth rate of the isolated strain, 5 uL of the precultured strain was inoculated to 100 mL of a urea liquid medium, and the resultant was shake-cultured in a shaking incubator (28° C., 160 rpm). During the culturing, 1 mL of culture liquid taken at 0, 4, 8, 12, 24, 30, 36, 48, 60, and 72 hour was subjected to absorbance measurement at 600 nm with a spectrophotometer (DR/4000U spectrophotometer, HACH).

(2) Analysis of Contamination Degree and Characteristic of Soil for Isolating Strain To investigate heavy metal contamination degrees of soil in mine areas collected for isolation of a strain, heavy metal content in the soil was measured through an aqua regia extraction method. For the experiment to investigate heavy metal content, soil which was dried and sieved with a 2 mm sieve was used. 3 g of soil, 21 mL of 35% HCl, 7 mL of 70% $HNO_3$ were added to a 250 mL reaction vessel. Then, 15 mL of 0.5 M $HNO_3$ was added to an absorption vessel. Then, the absorption vessel and a reflux cooling tube were coupled to the reaction vessel and maintained for 2 hours to allow organic substances to be slowly oxidized. Then, temperature was gradually increased to reach the reflux condition and maintained 2 hours. After degradation was completed, the reaction vessel was cooled. The content in the absorption vessel was added to the reaction vessel via the reflux cooling tube. The absorption vessel and reflux cooling tube were washed with 0.5 M $HNO_3$ and placed into the reaction vessel.

The resultant was filtered with a "Whatman" No. 40 filter to 100 mL volume flask, and insoluble remainders were washed by using a minimal amount of 0.5M $HNO_3$ on the filter. Then, the flask was filled with 0.5M $HNO_3$ to reach about 100 mL and cold-stored. The analytic sample thus prepared was diluted using distilled water and then analyzed with Inductively Coupled Plasma-Atomic Emission Spectrometer (ICP-AES, ULTIMA2, Horiba). Further, the soil used to isolate the strain was characterized. 4 g of soil and 40 mL of deionized water were added to a 50 mL centrifuge tube, and the tube was shaken for 6 hours with 150 rpm. After the reaction, the resultant was centrifuged for 3 minutes with 2000 rpm, and the supernatant was filtered by using a 0.45 μm membrane filter. In the filtered solution thus obtained, pH and electric conductivity (EC) were measured by using pH/COND METER (D-54, Horiba).

(3) Measurement of Urease Activity of Isolated Strain

To measure the urease activity of isolated bacterial strains, the precultured strains were inoculated to 100 mL of a urea liquid medium, and the resultant was shake-cultured for 72 hours at 28° C. with 160 rpm. The strain was obtained through centrifugation (4° C., 7,000×g) for 10 minutes. Pellet washing was performed twice with 50 mM sodium phosphate (pH 7.5). Then, the strain was suspended with a lysis buffer (50 mM sodium phosphate-1 mM EDTA, pH 7.5). The suspended strain was lysed for 10 minutes with a sonicator (Analog Sonifier Model-450, BRANSON) which was set to have output control 3, and duty cycle 70. The lysed strain was centrifuged (4° C., 10,000×g) for 20 minutes to obtain supernatant which was used as a reaction liquid for measuring the urease activity. To analyze ammonia content for measuring the urease activity, used was the indophenol method of "Weatherburn" in which color development degrees exhibited by indophenol, which was produced when ammonia was reacted with phenol-hypochlorite was measured as absorbance at 630 nm. For urease reaction, 3 mL of 10 mM urea solution and 10 μL of reaction liquid were added, mixed and allowed to react at 30° C. for 5 minutes. The reaction was terminated by adding 2 mL phenol-nitroprusside and 2 mL alkaline hypochlorite to the enzymatic reaction liquid and heating the reactant in boiled water at 60° C. for 10 minutes. Then, absorbance was measured at 630 nm. The urease activity was quantified with a standard curve obtained from prepared $NH_4Cl$ diluted solution. 1 unit of the urease activity was defined as an amount of the enzyme required to hydrolyze 1 μmol of urea per minutes by using urea as substrate.

(4) Investigation of Ability to Produce $CaCO_3$

To investigate $CaCO_3$ precipitates produced by the isolated strains, 1 mL of preculture was inoculated to 400 mL of a urea liquid medium, and the resultant was shake-cultured at 28° C. with 160 rpm. To compare quantity of produced precipitates with lapse of time, 25 mL of culture liquid was collected for every 12 hours of culturing for 96 hours in total, and the culture liquid was centrifuged (4° C., 12,000×g) for 10 minutes to remove supernatant. The obtained strain and precipitate were dried for 24 hours in a 50° C. dry oven and stored, and then the resultants were taken out to measure weights. To morphological investigation of the produced $CaCO_3$ precipitate, analysis was performed by using scanning electron microscope (SEM, JSM-7000F, Jeol) and energy dispersive spectrometer (EDS). After completely drying each sample, the sample was prepared in a 0.5 cm cube pieces and observed through a platinum sputter coating.

2. Experimental Result (1) Isolation and Identification of Strain Having Urease Activity To isolate a strain producing urease in soil surrounding an exhausted metalliferous mine area contaminated with heavy metals, a colony obtained by being inoculated to a urea liquid and solid medium, cultured and then subjected to selective enrichment of 5 steps was pure-isolated. Total 12 colonies were pure-isolated, and base sequences of 16S rRNA genes were sequenced. As a result of searching homology of the base sequences of the 16S rRNA genes of the isolated strains through blast, 7 *Sporosarcina* sp., 2 *Virgibacillus* sp., and 3 *Bacillus* spp. were found. Among 12 strains, 3 strains which have rapid growth rates and relatively good abilities to produce $CaCO_3$ were selected, respectively named as *Sporosarcina* sp. KM-01, *Sporosarcina* sp. KM-07, and *Sporosarcina* sp. KM-12 strains and deposited to "KCTC".

The selected strains were subcultured 10 times, and then base sequences of 16S rRNA genes were analyzed again. Consequently, strains respectively show homology with the *Sporosarcina pasteurii* strain of 98.87% (KM-01), 99.67% (KM-07), and 99.21% (KM-12). FIG. 1 shows a result of preparing a phylogenetic tree for these 3 strains. In FIG. 1, those denoted as 12, 1, 7 respectively indicate the KM-12, KM-01 and KM-07 strains.

All of 3 strains showed high homology with *Sporosarcina pasteurii*, and also had high relation with the *Sporosarcina siberiensis* strain. In the typical study, strains having abilities to produce $CaCO_3$ were mainly isolated from general soil without contaminants such as heavy metals or organic substances. However, since bacterial strains isolated by the present study were isolated from soil contaminated with high concentration of heavy metals and having strong acidity, and the survival thereof was confirmed, it can be expected that the strains have developed specific survival and evolution due to various organic/inorganic substances remained for a long period of time and continuous weathering, and the strains were considered as examples showing diversity of soil microorganisms.

(2) Analysis of Contamination Degree and Characteristic of Soil for Isolating Strain To investigate heavy metal contamination degrees of collected soil in an exhausted mine area, the collected soil sample was pretreated and then quantitative and qualitative analysis for heavy metals was performed through ICP-AES analysis. Consequently, several types of heavy metals were detected. Species relatively in high concentration, which exceeds 10 mg $kg^{-1}$, were Mn (170.50 mg $kg^{-1}$), As (114.05 mg $kg^{-1}$), Zn (92.07 mg $kg^{-1}$), Cu (62.44 mg $kg^{-1}$), and Pb (40. mg $kg^{-1}$) (see the table in FIG. 2). All heavy metal species described above have concentration above 40 mg $kg^{-1}$ so that it has been found that the soil was severely contaminated with heavy metals. In particular, Mn and As have concentration above 100 mg $kg^{-1}$, indicating a typical exhausted metalliferous mine soil having high degree of contamination.

As the analytic result, soil in the closed and exhausted mine area has remarkable As contamination in most cases, and also is contaminated with heavy metals such as Mn, Zn, Pb, Cu, and Cd due to release of water in the mine and loss of tailing generated during processes such as refining.

Since the strains having urease activity isolated in the present study are expected to have resistance to various heavy metals as well as an ability to precipitate calcium carbonate, thereby having a potential to be widely applied to various fields in remediation of contaminated soil in such a form. To characterize the soil, pH and EC were measured. Consequently, it has been found that pH of the soil was 2.66, which indicates strong acidic soil. Also, through EC measurement result, it has been found that the soil was mineralized because the EC value was higher than that of farmlands in Korea (see the table in FIG. 2). As a result of measuring pH and EC, it has been found that the soil used in the experiment to isolate strains was soil derived from relatively extreme environment.

(3) Investigation of Growth Rate of Isolated Strain

To investigate characteristics and differences in growth rates of 3 strains such as *Sporosarcina* sp. KM-01, KM-07, and KM-12 strains isolated in the present study, growth rate investigation was performed. Consequently, until 8 hours of culturing after inoculation, there was no difference in growth rates between strains. However, after 12 hours of culturing, the KM-01 strain showed rapid growth rate than KM-07 and KM-12 strains, and growth was continued thereafter. Meanwhile the KM-07 strain showed relatively slow growth rate than the KM-01 strain or KM-12 strains, but showed steady increase in cell turbidity value (see the graph in FIG. 3). In addition, in the present experiment to investigate growth rate, for all strains, it has been shown that the lag phase grows rapidly and shortly through inoculation after preculture. By applying this characteristic to applied research for substantially contaminated areas, it has been determined that a rapid effect on stabilization of soil or stabilization of heavy metals would be expected.

Figure 3:
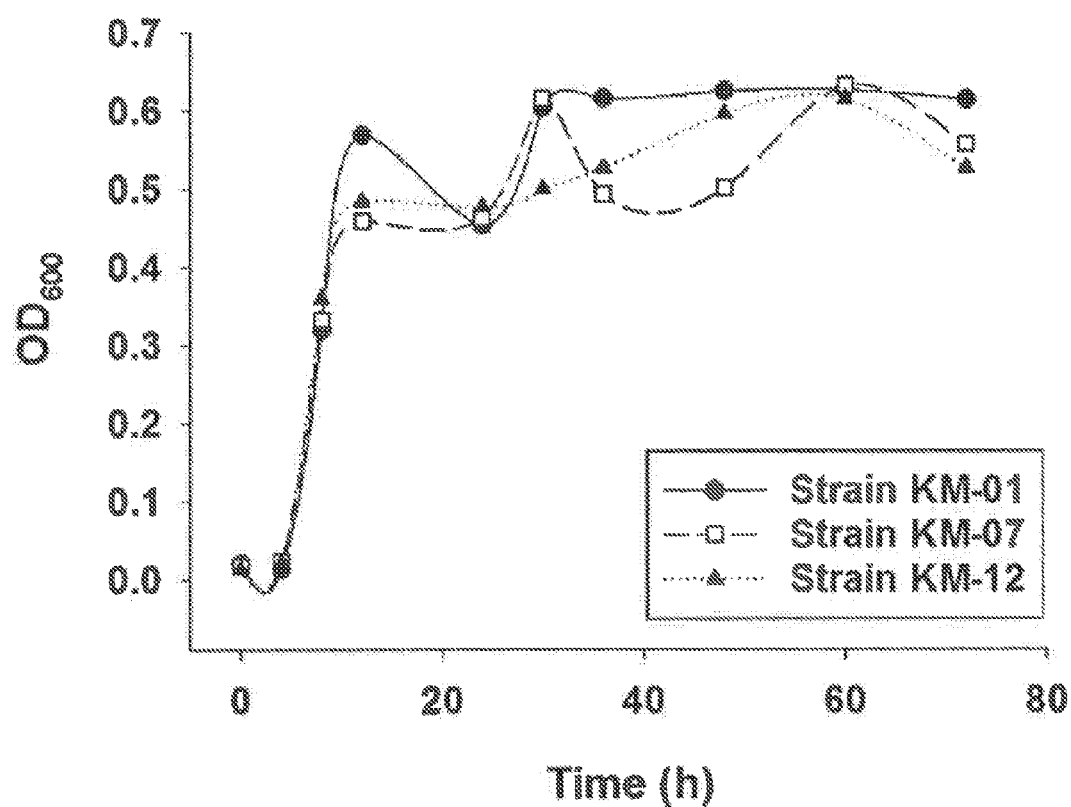
FIG. 3 is a graph showing a result of an experiment to investigate growth rates for 3 strains isolated by the present researchers.

As shown in the graph in FIG. 3, growth of each strain was likely to be continuously maintained until 72 hours after inoculation. Also, it is expected that, through repetitive inoculation at the time point when the growth curve is decreased, the activity can be maintained for a long period of time and efficiency can be enhanced.

(4) Measurement of Urease Activity of Isolated Strain

Figure 4:
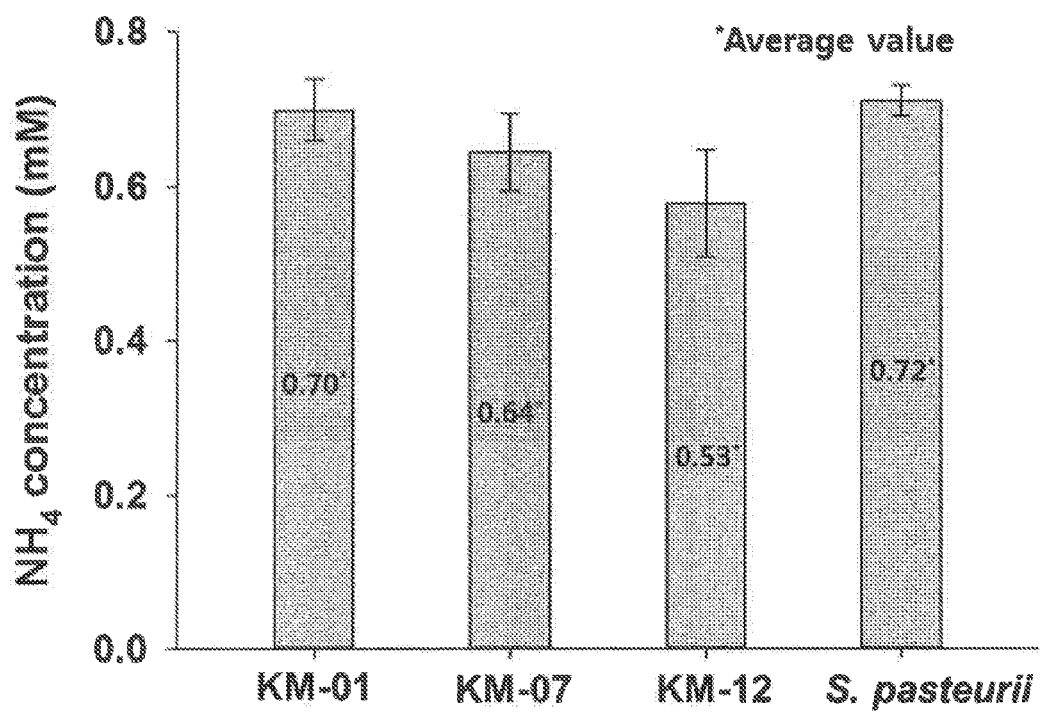
FIG. 4 is a graph showing a result of experimenting urease activities for 3 strains and the *Sporosarcina pasteurii* standard strain.

To directly investigate whether the bacterial strains isolated from soil in an exhausted mine area substantially have biochemical enzyme, i.e., urease activity, crude enzyme extracts were respectively extracted from the isolated *Sporosarcina* sp. KM-01, KM-07, and KM-12 strains, and a standard strain, i.e., *Sporosarcina pasteurii* KCTC3558 which was provided and used as a control. Then, urease activities were measured and compared through ammonia content by using the indophenol method of Weatherburn. Consequently, as shown in the graph in FIG. 4, the ammonia concentrations, which indicate activities of the isolated strains, were measured as KM-01 (0.70 mM), KM-07 (0.64 mM), and KM-12 (0.53 mM). For the standard strain *Sporosarcina pasteurii* KCTC3558 used as a positive control, the ammonia concentration was 0.72 mM which was similar level to those of the isolated strains. In particular, the KM-01 strains showed an almost equivalent level of activity as that of the control strain, *Sporosarcina pasteurii* KCTC3558, indicating the highest activity among the isolated strains as the growth rate experimental result above. Through these result, it has been found that the isolated strains have similar tendency of growth and urease activity when compared to the standard strain and the isolated strain has an extremely high activity.

(5) Investigation of Ability to Produce $CaCO_3$

Figure 5:
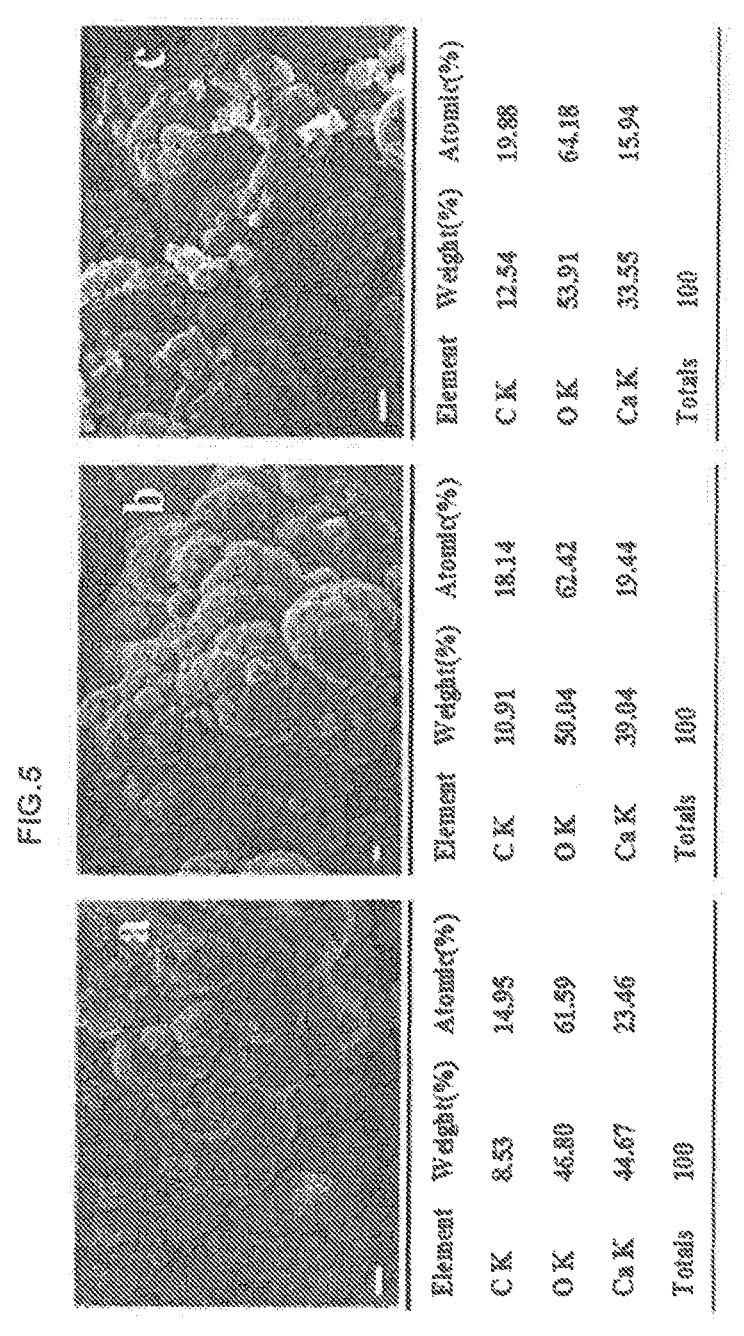
Figure 6:
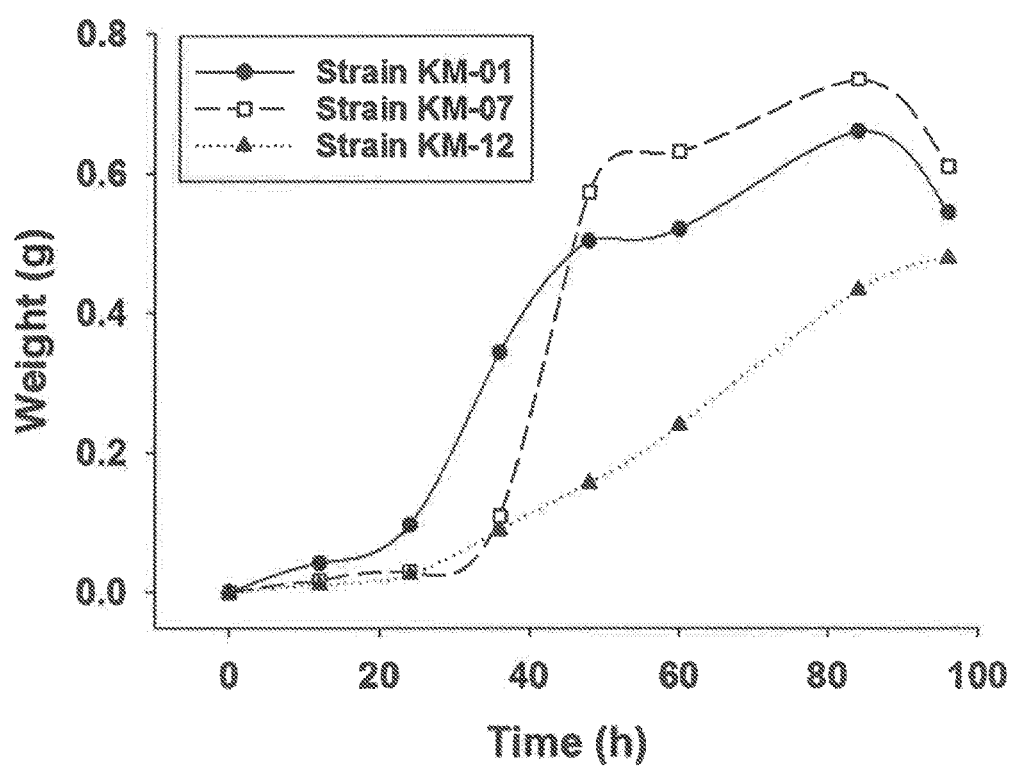
FIG. 6 is a graph obtained by measuring changes in weights with lapse of time for sample precipitates analyzed by SEM-EDS.

For $CaCO_3$ precipitation of the strains isolated from an exhausted mine area, strains were cultured in a urea medium into which calcium chloride ($CaCl_2$) was added. $CaCO_3$ produced by urease produced from the strains was investigated through electron microscopy (SEM) and EDS element analysis (see FIG. 5). The weight of the sample precipitate analyzed with SEM-EDS was measured. Consequently, the weights tended to be increased with lapse of time in all of 3 strains (see the graph in FIG. 6). As shown in SEM-EDS result performed to investigate $CaCO_3$ precipitation, after culturing of each strain, a precipitate including only C, O, and Ca was found. Also, $CaCO_3$ precipitation was morphologically observed. For the KM-01 strain, quantity of the produced precipitate was rapidly increased after 24 hours. For the KM-07 strain, quantity of the precipitate was likely to increase after 36 hours. Meanwhile, for the KM-12 strain, it has been found that, unlike the KM-01 and KM-07 strains, there was no time point when the precipitate rapidly increased and instead quantity of the precipitate was gradually increased. Comparing these result to the growth curve (FIG. 3) and urease activity measurement result (FIG. 4) of each strain, it has been found that the activity of the KM-01 strain was most active in this condition. Further, it is assumed that decrease in quantity of the precipitate after 96 hours is caused by depletion of a calcium source and nutrients added in the medium. Therefore, it has been found that 3 strains isolated from soil of an exhausted mine area contaminated with high concentration of heavy metals can produce $CaCO_3$ precipitates by the action of $CaCl_2$ used as a calcium source and urease.

It has been expected that the activities of the bacterial strains isolated by the present study are usefully applied to a remediation study in which the biochemical reaction is applied to remediation of soil of closed/exhausted mine areas contaminated with heavy metals.

[Accession Number]

Deposition organization: Korea Research Institute of Bioscience and Biotechnology Accession number: KCTC12800BP Deposition date: 27 Apr. 2015

Deposition organization: Korea Research Institute of Bioscience and Biotechnology Accession number: KCTC12801BP Deposition date: 27 Apr. 2015

Deposition organization: Korea Research Institute of Bioscience and Biotechnology Accession number: KCTC12802BP Deposition date: 27 Apr. 2015

According to the present invention, the novel *Sporosarcina* sp. strain produces urease by the metabolic activity, and then the urease hydrolyzes urea to thereby produce a carbonic acid. Thereafter, the carbonic acid reacts with calcium in soil to thereby precipitate calcium carbonate in the soil. During the course of calcium carbonate precipitation, heavy metals are adsorbed in and coprecipitated with calcium carbonate, and mobility thereof is declined, so that heavy metals are stabilized. Further, there is an advantage in that calcium carbonates fills pores in soil, thereby caking the soil, so that the soil is prevented from loss and the soil is reinforced.

Therefore, without periodically providing separate urease in exhausted mine areas, calcium carbonate precipitation continuously occurs due to the microorganism strain, so that contaminated soil may be stably remediated.

Further, an ammonium ion generated during degradation of urea by urease increases pH of the soil and neutralizes the acidic soil.

What is claimed is:

1. A method for remediating contaminated soil, comprising:
inoculating, soil which is contaminated with heavy metals, with a *Sporosarcina* sp. KCTC 12800BP strain which includes a base sequence of SEQ ID NO: 1 which produces urease.

2. The method of claim 1, further inoculating the soil with a *Sporosarcina* sp. KCTC 12801BP strain which includes a base sequence of SEQ ID NO: 2 which produces urease.

3. The method of claim 1, further inoculating the soil with a *Sporosarcina* sp. KCTC 12802BP strain which includes a base sequence of SEQ ID NO: 3 which produces urease.

4. The method of claim 1, wherein the *Sporosarcina* sp. KCTC 12800BP strain is isolated from acidic soil contaminated with heavy metals in an exhausted mine area.

5. The method of claim 1, further comprising spreading urea onto the soil prior to the inoculating step.

6. The composition for remediating contaminated soil of claim 1, further comprising a calcium agent.

7. The method of claim 1, comprising additionally providing urease to the soil.

8. The method of claim 7, wherein the additionally provided urease is extracted from bean juice.

9. The method of claim 1 wherein the *Sporosarcina* sp. KCTC 12800BP strain inoculated in the soil produces urease which hydrolyzes urea in the soil in which generates a carbonate ion in which the carbonate ion reacts with a calcium ion in the soil to precipitate calcium carbonate, thereby stabilizing heavy metals in the soil and neutralizing a pH of the soil.

10. The method of claim 1, further comprising re-inoculating the soil with the *Sporosarcina* sp. KCTC 12800BP strain after the inoculating step.

11. The method of claim 10, wherein the re-inoculating step is performed 72 hours after the inoculating step.

12. The method of claim 10, wherein the re-inoculating step is performed after 72 hours subsequent to the inoculating step.

13. A method for remediating contaminated soil, comprising:
inoculating the soil with a *Sporosarcina* sp. KCTC 12800BP strain, a *Sporosarcina* sp. KCTC 12801BP strain, and a *Sporosarcina* sp. KCTC 12802BP strain, wherein
the *Sporosarcina* sp. KCTC 12800BP strain includes a base sequence of SEQ ID NO: 1,
the *Sporosarcina* sp. KCTC 12801BP strain includes a base sequence of SEQ ID NO: 2, and
the *Sporosarcina* sp. KCTC 12802BP strain includes a base sequence of SEQ ID NO: 3.

14. The method of claim 13, further comprising adding urea onto the soil.

15. The method of claim 13, further comprising providing urease onto the soil.

16. The method of claim 13, further comprising spreading calcium chloride onto the soil.

17. The method of claim 13, further comprising re-inoculating the soil with the *Sporosarcina* sp. KCTC 12800BP strain, the *Sporosarcina* sp. KCTC 12801BP strain, and the *Sporosarcina* sp. KCTC 12802BP strain subsequent to the inoculating step.

18. The method of claim 16, wherein the re-inoculating step is performed 72 hours subsequent to the inoculating step.

19. The method of claim 16, wherein the re-inoculating step is performed after 72 hours subsequent to the inoculating step.

20. A method for remediating contaminated soil, comprising:
inoculating the soil with a *Sporosarcina* sp. KCTC 12800BP strain, a *Sporosarcina* sp. KCTC 12801BP strain, and a *Sporosarcina* sp. KCTC 12802BP strain, wherein
the *Sporosarcina* sp. KCTC 12800BP strain includes a base sequence of SEQ ID NO: 1,
the *Sporosarcina* sp. KCTC 12801BP strain includes a base sequence of SEQ ID NO: 2, and
the *Sporosarcina* sp. KCTC 12802BP strain includes a base sequence of SEQ ID NO: 3;
adding urea onto the soil;
providing urease onto the soil;
spreading calcium chloride onto the soil; and
re-inoculating the soil with the *Sporosarcina* sp. KCTC 12800BP strain, the *Sporosarcina* sp. KCTC 12801BP strain, and the *Sporosarcina* sp. KCTC 12802BP strain subsequent to the inoculating step.

* * * * *

SEQUENCE LISTING

```
<160> NUMBER OF SEQ ID NOS: 5

<210> SEQ ID NO 1
<211> LENGTH: 1483
<212> TYPE: DNA
<213> ORGANISM: Sporosarcina sp.

<400> SEQUENCE: 1
ctcaggacga acgctggcgg cgtgcctaat acatgcaagt cgagcgaaca gacgaggagc      60
ttgctcctct gacgttagcg gcggatgggt gagtaacacg tgggcaacct gccctgcagt     120
tggggataac tccgggaaac cggggctaat accgaataat cagttccttc gcatgaagga     180
actctgaaag acggctatgc tgtcactgca ggatgggccc gcggcgcatt agctagttgg     240
tgaggtaacg gcttaccaag gcgacgatgc gtagccgacc tgagagggtg atcggccaca     300
```

```
ctgggactga gacacggccc agactcctac gggaggcagc agtagggaat cttccacaat      360
ggacgaaagt ctgatggagc aacgccgcgt gagcgaagaa ggttttcgga tcgtaaagct      420
ctgttgtgag gaagaacaa gtacaggagt aactgtctgt accttgacgg tacctcatta       480
gaaagccacg gctaactacg tgccagcagc cgcggtaata cgtaggtggc aagcgttgtc      540
cggaattatt gggcgtaaag cgcgcgcagg cggcctttta agtctgatgt gaaagcccac      600
ggcttaaccg tggaaggtca ttggaaactg aaggcttga gtacagaaga ggaaagcgga      660
attccacgtg tagcggtgaa atgcgtagag atgtggagga acaccagtgg cgaaggcggc      720
tttctggtct gtaactgacg ctgaggcgcg aaagcgtggg gagcaaacag gattagatac      780
cctggtagtc cacgccgtaa acgatgagtg ctaagtgtta gggggtttcc gccccttagt      840
gctggagcaa acgcattaag cactccgcct ggggagtacg gccgcaaggc tgaaactcaa      900
aggaattgac ggggacccgc acaagcggtg gagcatgtgg tttaattcga agctacgcga     960
agaaccttac caggtcttga catcccgctg cccggtatag agatatacct ttcccttcgg    1020
ggacagcggt gacaggtggt gcatggttgt cgtcagctcg tgtcgtgaga tgttgggtta    1080
agtcccgtaa cgagcgcaac ccttgacctt agttgccagc attcagttgg cactctaag    1140
gtgactgccg gtgacaaacc ggaggaaggt ggggatgacg tcaaatcatc atgcccctta    1200
tgacctgggc tacacacgtg ctacaatgga cggtacagag ggttgccaac ccgcgagggg    1260
gagctaatcc cataaaaccg ttcccagttc ggattgcagg ctgcaactcg cctgcatgaa    1320
gcaggaatcg ctagtaatcg tggatcagca tgccacggtg aatacgttcc ccgggtcttg    1380
tacacacccg cccgtcacac cacgaagagt ttgtaacacc cgaaagtcgg tgggggtaac    1440
cctttttggg agccagccgc ccaaagtggg acaaataat tgg                        1483

<210> SEQ ID NO 2
<211> LENGTH: 1525
<212> TYPE: DNA
<213> ORGANISM: Sporosarcina sp.

<400> SEQUENCE: 2
tcctgctcag gacgaacgct ggcggcgtgc ctaatacatg caagtcgagc gaacagacga      60
ggagcttgct cctctgacgt tagcggcgga tgggtgagta acacgtgggc aacctgccct     120
gcagatgggg ataactccgg gaaaccgggg ctaataccga ataatcagtt ccttcgcatg     180
aaggaactct gaaagacggc tatgctgtca ctgcaggatg ggcccgcggc gcattagcta     240
gttggtaagg taacggctta ccaaggcgac gatgcgtagc cgacctgaga gggtgatcgg     300
ccacactggg actgagacac ggcccagact cctacgggag gcagcagtag ggaatcttcc     360
acaatggacg aaagtctgat ggcaacgc cgcgtgagcg aagaaggttt tcggatcgta     420
aagctctgtt gtgagggaag aacaagtaca ggagtaactg tctgtacctt gacggtacct     480
cattagaaag ccacggctaa ctacgtgcca gcagccgcgg taatacgtag gtggcaagcg    540
ttgtccggaa ttattgggcg taaagcgcgc gcaggcggcc ttttaagtct gatgtgaaag    600
cccacggctc aaccgtggaa ggtcattgga aactggaagg cttgagtaca agaggaaa       660
gcggaattcc acgtgtagcg gtgaaatgcg tagagatgtg gaggaacacc agtgcgaag     720
gcggctttct ggtctgtaac tgacgctgag gcgcgaaagc gtgggagca acaggatta      780
gatacctgg tagtccacgc cgtaaacgat gagtgctaag tgttagggg ttccgcccc      840
ttagtgctgg agcaaacgca ttaagcactc cgcctgggga gtacgccgc aaggctgaaa     900
```

| | |
|---|---|
| ctcaaaggaa ttgacgggga cccgcacaag cggtggagca tgtggtttaa ttcgaagcta | 960 |
| cgcgaagaac cttaccaggt cttgacatcc cgctgcccgg tgtagagata cgccttccc | 1020 |
| ttcggggaca gcggtgacag gtggtgcatg gttgtcgtca gctcgtgtcg tgagatgttg | 1080 |
| ggttaagtcc cgtaacgagc gcaacccttg accttagttg ccagcattca gttgggcact | 1140 |
| ctaaggtgac tgccggtgac aaaccggagg aaggtgggga tgacgtcaaa tcatcatgcc | 1200 |
| ccttatgacc tgggctacac acgtgctaca atggacggta cagagggttg ccaacccgcg | 1260 |
| aggggggagct aatcccagaa aaccgttccc agttcggatt gcaggctgca actcgcctgc | 1320 |
| atgaagcagg aatcgctagt aatcgtggat cagcatgcca cggtgaatac gttcccggg | 1380 |
| tcttgtacac cccgcccgt caccaccacg agagtttgta acacccgaaa gtcggtgggg | 1440 |
| gtaacccttt ttgggagcca gccgcccaaa gtgggacaaa ataattgggg tgaactagga | 1500 |
| gaaaaacccc cacacacaca caaaa | 1525 |

<210> SEQ ID NO 3
<211> LENGTH: 1481
<212> TYPE: DNA
<213> ORGANISM: Sporosarcina sp.

<400> SEQUENCE: 3

| | |
|---|---|
| caggacgaac gctggcggcg tgcctaatac atgcaagtcg agcgaacaga tgaggagctt | 60 |
| gctcctctga cgttagcggc ggatgggtga gtaacacgtg gcaacctgcc ctgtagttg | 120 |
| gggataactc cgggaaaccg gggctaatac cgaataatta gtttcttcgc atgaaggaac | 180 |
| tctgaaagac ggctatgctg tcactacagg atgggcccgc ggcgcattag ctagttggtg | 240 |
| gggtaatggc ctaccaaggc gacgatgcgt agccgacctg agagggtgat cggccacact | 300 |
| gggactgaga cacggcccag actcctacgg gaggcagcag tagggaatct tccacaatgg | 360 |
| acgaaagtct gatggagcaa cgccgcgtga gcgaagaagg ttttcggatc gtaaagctct | 420 |
| gttgtgaggg aagaacaagt acaggagtaa ctgtctgtac cttgacggta cctcattaga | 480 |
| aagccacggc taactacgtg ccagcagccg cggtaatacg taggtggcaa cgttgtccg | 540 |
| gaattattgg gcgtaaagcg cgcgcaggcg gccttttaag tctgatgtga agcccacgg | 600 |
| cttaaccgtg gaaggtcatt ggaaactgga aggcttgagt acagaagagg aaagcggaat | 660 |
| tccacgtgta gcggtgaaat gcgtagagat gtggaggaac accagtggcg aaggcggctt | 720 |
| tctggtctgt aactgacgct gaggcgcgaa agcgtgggga gcaaacagga ttagataccc | 780 |
| tggtagtcca cgccgtaaac gatgagtgct aagtgttagg gggtttccgc cccttagtgc | 840 |
| tggagcaaac gcattaagca ctccgcctgg ggagtacggt cgcaagactg aaactcaaag | 900 |
| gaattgacgg ggacccgcac aagcggtgga gcatgtggtt taattcgaag ctacgcgaag | 960 |
| aaccttacca ggtcttgaca tcccgctgac cggtatagag atatacccttt ccctttcgggg | 1020 |
| acagcggtga caggtggtgc atggttgtcg tcagctcgtg tcgtgagatg ttgggttaag | 1080 |
| tcccgtaacg agcgcaaccc ttgaccttag ttgccagcat tcagttgggc actctaaggt | 1140 |
| gactgccggt gataaaccgg aggaaggtgg ggatgacgtc aaatcatcat gccccttatg | 1200 |
| acctgggcta cacacgtgct acaatggatg gtacagaggg ttgccaaccc gcgaggggga | 1260 |
| gctaatccca taaaaccatt cccagttcgg attgcaggct gcaactcgcc tgcatgaagc | 1320 |
| aggaatcgct agtaatcgtg gatcagcatg ccacggtgaa tacgttcccg ggtcttgtac | 1380 |
| accccgcccg tcacaccacg agagtttgt aacacccgga agtcggtggg ggtaacccttt | 1440 |
| tttgggagcc agcccccccaa aggtgggaca aaatgattgg g | 1481 |

```
<210> SEQ ID NO 4
<211> LENGTH: 20
<212> TYPE: DNA
<213> ORGANISM: Artificial Sequence
<220> FEATURE:
<223> OTHER INFORMATION: 518F which is a primer

<400> SEQUENCE: 4
ccagcagccg cggtaatacg                                               20

<210> SEQ ID NO 5
<211> LENGTH: 18
<212> TYPE: DNA
<213> ORGANISM: Artificial Sequence
<220> FEATURE:
<223> OTHER INFORMATION: 800R which is a primer

<400> SEQUENCE: 5
taccagggta tctaatcc                                                 18
```